United States Patent [19]

Glatzer

[11] 3,995,619

[45] Dec. 7, 1976

[54] COMBINATION SUBCUTANEOUS SUTURE REMOVER, BIOPSY SAMPLER AND SYRINGE

[76] Inventor: Stephen G. Glatzer, 541 Pelham Road, New Rochelle, N.Y. 10805

[22] Filed: Oct. 14, 1975

[21] Appl. No.: 622,162

[52] U.S. Cl. .......................... 128/2 B; 128/303 R; 128/305; 128/346
[51] Int. Cl.² .................. A61B 10/00; A61B 17/00; A61B 17/32
[58] Field of Search ............... 128/2 B, 303 R, 305, 128/329, 346

[56] References Cited
UNITED STATES PATENTS

| | | | |
|---|---|---|---|
| 1,867,624 | 7/1932 | Hoffman | 128/2 B |
| 3,477,423 | 11/1969 | Griffith | 128/2 B |
| 3,877,434 | 4/1975 | Ferguson et al. | 128/346 X |
| 3,929,123 | 12/1975 | Jamshidi | 128/2 B |

Primary Examiner—Channing L. Pace
Attorney, Agent, or Firm—Lackenbach, Lilling & Siegel

[57] ABSTRACT

A multi-purpose surgical instrument for subcutaneous use is described. The instrument includes a generally hollow inner tube which is provided at a probing free end with a crochet-type hook. The other end, or hand-held end, is fixedly joined to a finger grip. An inner clamping rod is slideably mounted within the hollow tube and can be selectively axially moved between clamping and releasing positions at the hook and be positively locked in the clamping condition thereof. An outside cutting sleeve receives the hollow tube therein and is provided with a rotary cutting edge which is adapted to angularly turn about the axis of the hollow tube to sweep at least a portion of the hook face to thereby cut an object clamped at the hook by the rod. A cutter actuator is connected to the outside cutting sleeve and cooperates with the handle finger grip to limit the relative angular turning or displacement between the hollow tube and the outside cutting sleeve to prevent the rotary cutting edge to sweep across the entire face of the hook. This assures that an object clamped within the hook is not totally released from the hook. By providing a helical-type cam-follower arrangement between the handle or finger grip and the cutter actuator, the cutting sleeve may be made to be linearly or axially displaced simultaneously with rotary or relative angular movement between the cutting sleeve and the hollow tube or hook. By utilizing only one, two or three of the operative members of the instrument, these being the hollow tube, elongate rod or outside cutting sleeve, the instrument may be utilized for different subcutaneous procedures.

37 Claims, 11 Drawing Figures

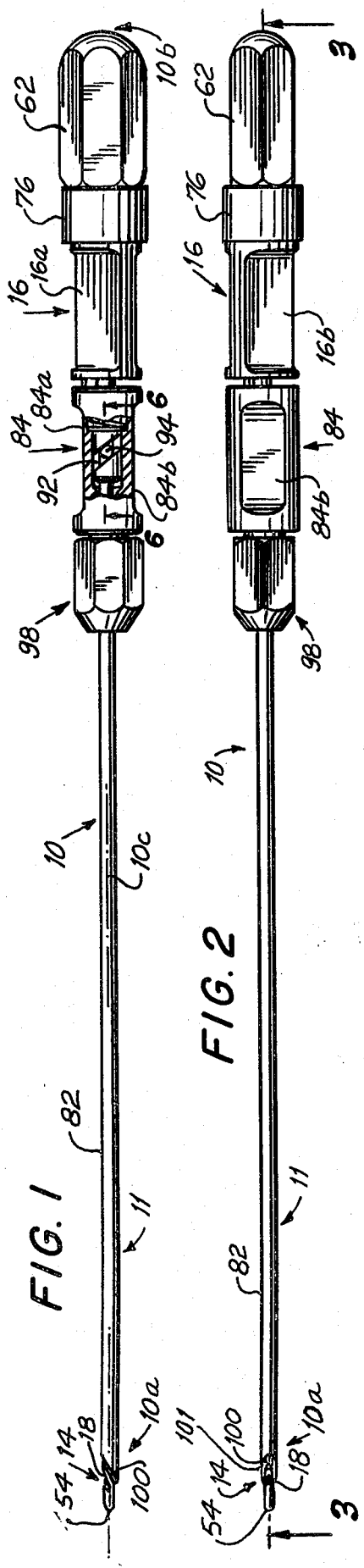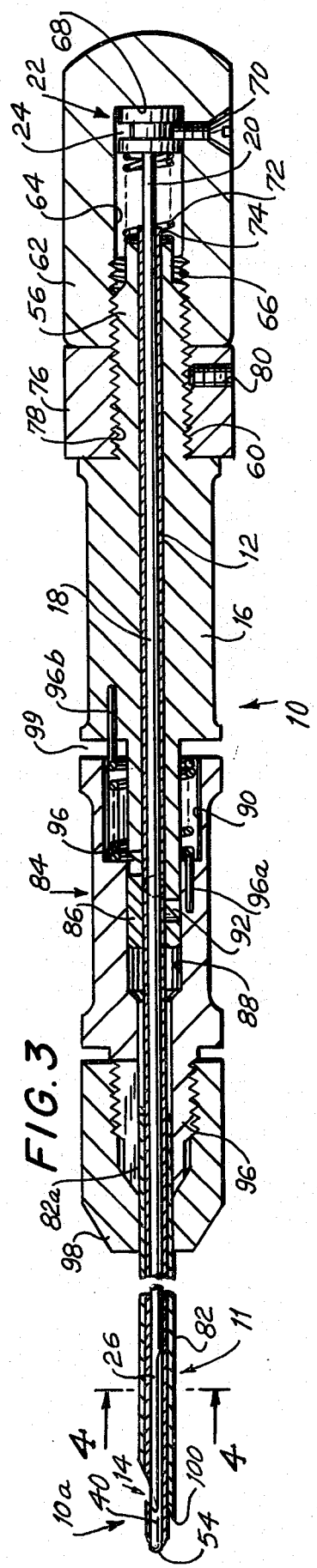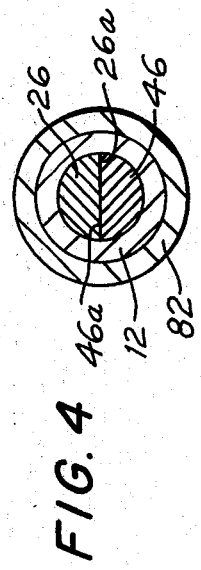

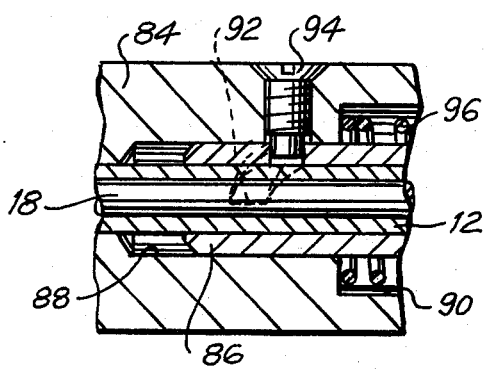
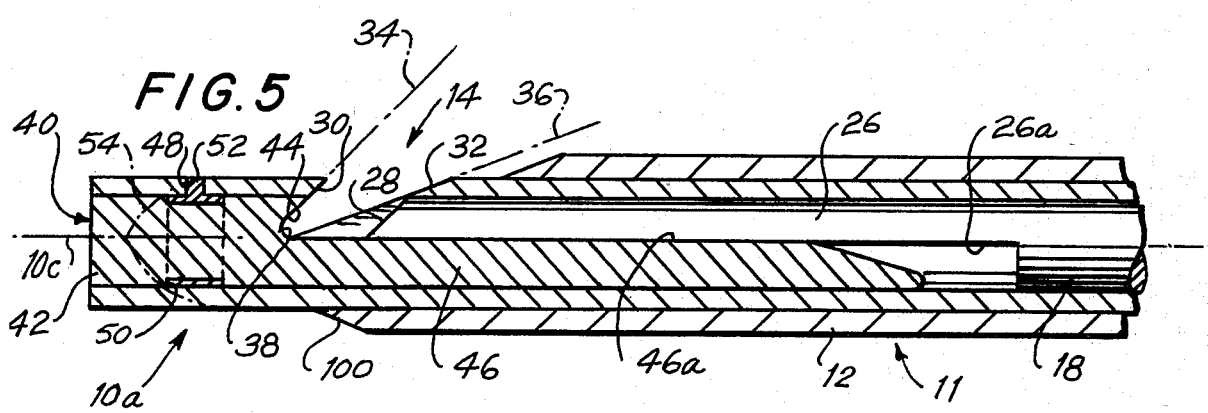
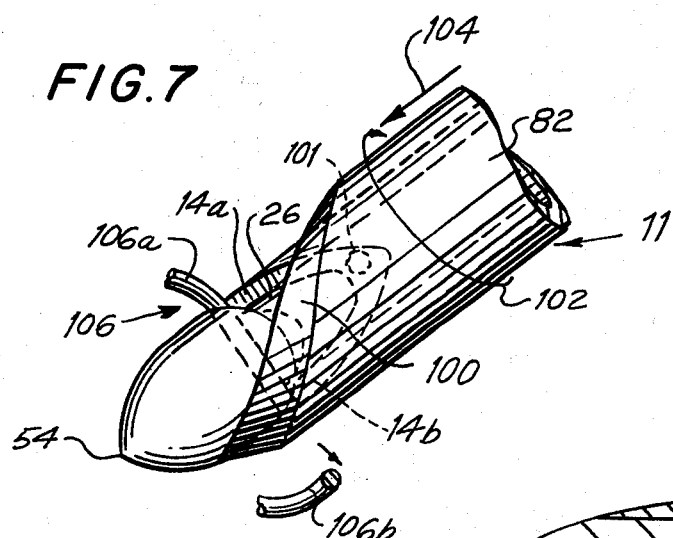
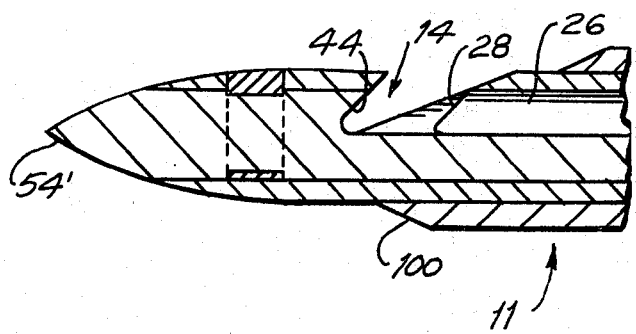

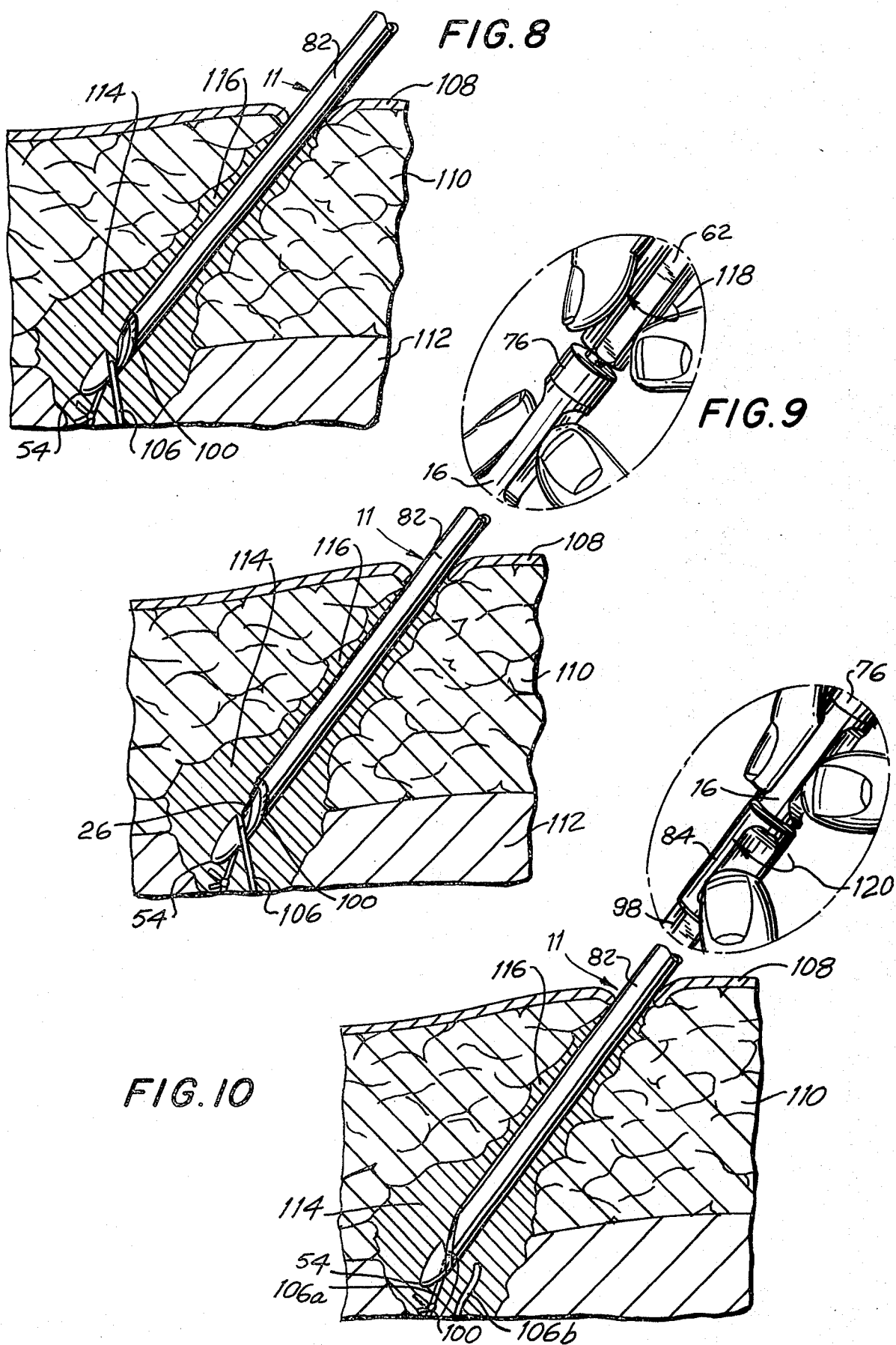

COMBINATION SUBCUTANEOUS SUTURE REMOVER, BIOPSY SAMPLER AND SYRINGE

BACKGROUND OF THE INVENTION

The present invention generally relates to surgical instruments, and more specifically to a combination multi-purpose instrument for subcutaneous use.

Perhaps the most frequent and most annoying complication of abdominal surgery is the wound which is commonly known as "spitting" silks. The presence of infected sinuses with non-absorbable sutures at their bases resulting in recurrent abscess formation is a painful and messy problem for the patient which often persists for months to years after the operation. The foreign body is finally extruded by the body or, preferably, extracted by the surgeon. After the suture is removed, the draining sinus closes permanently.

If the infected sutures cannot be removed from the sinuses, it may be necessary to excise the entire scar. This procedure in itself may not be entirely benign since the granuloma sinus may extend very close to the bowel, which is adherent to the scar on the peritoneal surface. Intestinal fistulas have been noted following excision of infected scars.

The extraction of sutures from granuloma sinuses has been accomplished traditionally by "fishing" for the suture in the infected sinus with either a hemostat or better with a small crochet-type hook. When the suture is hooked, it is drawn to the surface. Unfortunately, the suture may be deeply imbedded in the fascial layers and it cannot be extracted without first dividing it so that it can be pulled through the tissues. In order to divide it, the suture must be elevated to the skin surface to be visualized. This pulling may be quite painful for the patient. Also, when the crochet hook brings the suture to the surface for cutting, it must be grasped with, for example, a hemostat to prevent losing it back into the sinus after it is cut. Thus, three instruments are required to remove the embedded suture: a hook, a clamp, and a scissors or knife, and often two people are required to remove the suture from the sinus. It is often a very uncomfortable procedure for the patient, and if the patient is somewhat obese so that there are several centimeters of fat between the suture at the base of the sinus and the skin surface, it becomes impossible to remove the suture by this technique. Thus, surgical excision of the infected scar may be necessary.

Various surgical instruments have been proposed for solving some of the above problems. Examples of some of these instruments are disclosed in the following U.S. Pat. Nos. 3,328,876; 3,364,573; 3,443,313; 2,865,099; 2,127,190; 3,287,751; 2,041,521; 3,739,784; 3,791,387; 3,828,790. An examination of these patents reveals that most of these relate to hemostats or combination surgical instruments which are intended to cut and remove sutures. However, most of these are in the form of scissors or tweezers which have cutting and gripping portions so that a portion of the suture may be retained after cutting the same. Typical of the scissors-type instruments are disclosed in U.S. Pat. Nos. 2,127,190; 2,865,099; and 3,443,313. Typical of the tweezer-like instruments are disclosed in U.S. Pat. Nos. 3,328,876 and 3,364,573.

A common characteristic and disadvantage of the prior art suture removers is that the cutting and clamping is performed by portions of the instrument which move in directions generally normal to the axial or length direction of the instrument. Because of this requirement that the opposing tips or ends of the scissors or tweezers move laterally during fishing for the suture, the instruments could not be used in the smaller sinuses where there is insufficient space for such lateral movements. For this reason, as well as because the prior art instruments are not generally slender at the probing ends thereof, the prior art suture extractors are not normally used for subcutaneous procedures. As with the conventional procedures, the prior art instruments could be utilized when the sutures are near the skin surface or once the sutures are brought near that surface.

In U.S. Pat. No. 3,328,876, there is also disclosed a surgical suture extractor which includes a hook and a tubular member which is slideably mounted along the longitudinal axis of the instrument. The tubular member carries both a knife, which sweeps in the region of the hook, and a shoulder, which abuts against a side extension of the hook once the knife has been moved to the cutting position. However, since the cutting element and the clamping element are mounted for simultaneous movement on the same tubular member, positive locking is not possible so that even small axial movements of the tubular member subsequent to cutting of the suture results in release of the same. Additionally, the suture extractor being described is not in the nature of a slender probe which can be inserted through a narrow sinus to effect subcutaneous procedures.

Additionally, the proposed suture extractors of the prior art typically are limited in their usefulness to extracting sutures. In this respect, the prior art suture extractors do not include means for modifying the instruments so that they can be used for different purposes and possibly related procedures.

The instrument of the present invention is a multi-purpose combination surgical instrument for subcutaneous use which combines the hooking, clamping and cutting of the suture into one manipulation. Of even greater importance, the entire operation is done at the base of the sinus rather than on the skin surface, so that the sutures ten to twelve centimeters deep can be retrieved. This avoids the pain caused by pulling the sutures to the surface as has previously been required with the prior art instruments. Accordingly, the instrument of the present invention is an extremely useful item for a surgeon's office and may avoid the possible necessity of excising a scar with multiple infected granulomas.

By removing one or more of the elements of the combination surgical instrument of the present invention, the instrument can perform different functions to permit different subcutaneous procedures with basically the same instrument. The primary functions of the combination tool are as a subcutaneous suture remover, biopsy sampler and syringe.

SUMMARY OF THE INVENTION

Accordingly, it is an object of the present invention to provide a multi-purpose surgical instrument for subcutaneous use which overcomes the disadvantages above described in connection with the proposed prior art instruments.

It is another object of the present invention to provide a surgical instrument of the type under consideration which is simple in construction and economical to manufacture.

It is still another object of the present invention to provide a surgical instrument for subcutaneous use which is generally slender and can be inserted into and used in the narrowest of granuloma sinuses.

It is yet another object of the present invention to provide a surgical instrument of the type suggested in the above objects which can be used as a subcutaneous suture remover, biopsy sampler and syringe by slight modification of the instrument.

It is a further object of the present invention to provide a surgical instrument of the type under consideration which has an elongate and generally slender probe with a clamping arrangement at the probing free end thereof which includes cooperating elements which are mounted for movements along the general axis or length direction of the probe during movement between clamping and releasing positions.

It is still a further object of the present invention to provide a surgical instrument of the type under discussion which includes positive locking means for locking the clamping elements of the instrument in the gripping or clamping positions thereof to insure retention of at least a portion of an object such as a suture after cutting of the same so that the retained portion of the suture may be conveniently extracted.

It is an additional object of the present invention to provide a single surgical instrument which replaces two or more surgical instruments which have conventionally been utilized to perform the same subcutaneous suture extraction procedures.

It is an additional object of the present invention to provide a surgical instrument for performing subcutaneous procedures which can easily and conveniently be operated by a single person and which includes a plurality of coaxially arranged control elements which can be easily and conveniently gripped at the hand-held end of the instrument for operating the clamping and cutting elements at the probing free end thereof.

In order to achieve the above objects, as well as others which will become apparent hereafter, the multi-purpose surgical instrument for subcutaneous use in accordance with the present invention comprises probe means in the nature of an elongate and generally slender member having a generally uniform transverse cross-section along the longitudinal axis and having a bearing surface portion at the probing free end thereof. Clamping means is provided arranged for movement in a direction generally parallel to said axis of said probe means and having an end portion thereof movable between a first clamping position wherein said end portion abuts against said bearing surface portion and a second releasing position wherein said end portion is removed or spaced from said bearing surface portion. In this manner, said bearing surface portion and end portion together form a clamping device in the nature of a vise which can be opened and closed by relative movement therebetween along a direction generally parallel to said axis of said probe means. Advantageously, locking means is provided for positively locking the relative axial positions of said probe and clamping means in said first clamping position to prevent inadvertent release of an object being clamped. When used as a suture extractor or the like, the instrument is further provided with cutting means for cutting an object clamped by said probe and clamping means at only one clamped point at the clamping area. In this manner, at least a portion of the cut object is retained after cutting to permit subcutaneous extraction of that portion of the object which remains to be clamped. The relative movements of the probe means, clamping means and cutting means are controlled by a plurality of members which are coaxially disposed with said probe means and can easily and conveniently be gripped by the user to selectively control cutting or clamping operations at the probing end.

Because of the generally slender nature of the probe and the fact that the cutting and clamping operations do not require movements of portions of the instrument in directions normal to the axial direction thereof, the probing end of the instrument may be deeply inserted through the narrowest sinuses without the need for separating tissue during the cutting and clamping operations to thereby minimize the pain to the patient. All of the operations may be performed deep in the sinus near the base thereof and controlled and conveniently manipulated by a series of hand-held controls which can be easily gripped and moved relative to one another to effect the desired operations.

BRIEF DESCRIPTION OF THE DRAWINGS

Further advantages of the invention will become apparent from a reading of the following specification describing illustrative embodiments of the invention. This specification must be taken with the accompanying drawings of which:

FIG. 1 is a top plan view of the multi-purpose surgical instrument for subcutaneous use in accordance with the present invention, shown partly broken away to give some construction details of the device;

FIG. 2 is a side elevational view of the instrument shown in FIG. 1;

FIG. 3 is a longitudinal cross-section of the instrument shown in FIG. 2, taken along line 3—3;

FIG. 4 is a transverse section of the probe of the instrument shown in FIG. 3, taken along line 4—4;

FIG. 5 is an enlarged fragmented cross section of the free end of the probe of the instrument before the point is ground to provide a rounded end or tip, and showing one possible approach or method in the assembly and construction of the probe end which is particularly economical to manufacture;

FIG. 6 is an enlarged fragmented view, in elevation, of the cutter actuator element which is shown fragmented in FIG. 1;

FIG. 7 is a perspective view of the free end or tip of the probe, showing the rotary cutting edge angularly advanced with respect to the engaging hook to cut the suture only on one side of the clamping arrangement to maintain the other side of the suture clamped so that it can be extracted;

FIG. 8 is a section of the upper skin layers in which an incision has been made and where retaining sutures are embedded below the skin layers, showing the probing end of the instrument of the present invention extending through a relatively narrow granuloma sinus and to the base thereof to engage the suture which caused the infection;

FIG. 9 is similar to FIG. 8, but further showing the manner in which the instrument is manipulated in order to clamp the suture and positively lock the same within the clamp to prevent inadvertent escape thereof;

FIG. 10 is similar to FIG. 9, but is showing the manner in which the instrument controls are manipulated to effect a cutting action of the suture at only one of the clamped ends so that the other end of the suture remains clamped to the instrument for easy and convenient extraction from the sinus; and FIG. 11 is similar to FIG. 5, but showing the condition of the probe tip after the same has been ground, and further showing a slightly different, more pointed shape of the tip when the same is intended to be utilized as a hypodermic syringe which is pierced through the upper layers of the skin.

DESCRIPTION OF THE PREFERRED EMBODIMENTS

Referring now specifically to the figures, in which identical or similar parts are designated by the same reference numerals throughout, and first referring to FIGS. 1 and 2, the multi-purpose surgical instrument for subcutaneous use is generally designated by the reference numeral 10.

The surgical instrument 10 is elongate and has a probing end 10a and a hand-held end 10b. The instrument as a whole defines an axis 10c along which the probing and hand-held ends 10a and 10b are aligned.

The instrument 10 includes an elongate and generally slender probe 11 which has a generally uniform transverse cross-section along the longitudinal axis 10c thereof. While the probe 11 is shown to be cylindrical and having a uniform circular cross section along its length, it will be evident from the description that follows that the specific cross-sectional configuration is not critical for the purposes of the present invention. In order to permit insertion of the probe through the smallest of granuloma sinuses, it is only important that the probe 11 be made as slender as is practically possible in view of the desired capability for the instrument and the numerous procedures which are to be performed therewith.

The probe 11 includes a hollow tube 12, best shown in FIGS. 3–5, the length of the hollow tube 12 being selected to correspond with the anticipated depth of the penetration below the upper skin layers to effect subcutaneous procedures such as suture extraction. While the length of the hollow tube 12 can, therefore, be made only several inches long, the advantages of the instrument are best realized when the probe 11 is made substantially longer and in the range between 5 and 8 inches. However, as will become clear from the description that follows any desired length may be used with different degrees of advantage.

The hollow tube 12 is provided with a crochet-type hook which is generally designated by the reference numeral 14. The details of the hook 14 will be more described in connection with FIG. 5. As shown, the hook 14 is provided at the probing free end 10a of the probe 11.

The end of the hollow tube 12 which is remote from the hook 14 is joined or connected to a handle or a finger grip generally indicated by the reference numeral 16 which is coaxial with the hollow tube 12 and provided with a pair of flat surfaces 16a and 16b to facilitate grasping of the finger grip 16. Any suitable or conventional means may be used to fixedly connect the finger grip 16 to the hollow tube 12. For example, the finger grip 16 and hollow tube 12 may be soldered, welded, brazed or otherwise attached to each other in a relatively permanent fashion so that the hollow tube 12 follows all the movements of the finger grip 16 as will be more fully described hereafter. Disposed within the hollow tube 12 is a clamp rod 18 which is elongate as shown in FIG. 3, for example, and has external dimensions which correspond to the internal dimensions of the hollow tube 12 to leave little clearance therebetween yet allowing a slide fit so that the rod 18 can slidable and axially move with respect to the hollow tube 12.

The length of the clamp rod 18 is generally longer than that of the hollow tube 12 so that a portion or extension 20 of the clamp rod 18 normally projects axially beyond the hollow tube. The rod extension 20 is provided at one free end with a collar 22 which is in the nature of a cylindrical member as shown having an annular groove or recess 24, which groove is substantially uniform about the periphery of the collar 22 wherein the collar 22 takes on the appearance of a bobbin.

The rod 18 has an end remote from the extended end 20 and this remote end is designated by the reference numeral 26 which is in the region of hook 14. The clamping rod 18 is arranged for movement in a direction parallel to the axis 10c of the probe 11 and has the end 26 thereof movable between a clamping and a releasing position with respect to the hook 14, as will be more fully described hereafter.

The extreme tip of the end 26 is provided with a surface portion 28 which is inclined relative to the axis 10c as shown. The hook 14 is shown in FIG. 5 as generally being in the shape of a wedge-shaped transverse cut-out which opens in a direction away from the probing free end 10a and the direction of the hand-held portion 10b of the instrument 10. The wedge-shaped cut-out in the hollow tube 12 is defined by a pair of arcuate edges 30, 32 each of which respectively lies in one of two planes 34, 36 which intersect in the region of the axis along a line 38 substantially normal to the axis and each of which planes 34, 36 forms a different acute angle with the axis 10c and the major portion of the hollow tube 10b. In the presently preferred embodiment, the line of intersection 38 of the two planes 34, 36 passes near or through the axis 10c and is coincident with a diameter of the hollow tube 12.

Still referring to FIG. 5, there are shown the details for plugging up the end of the tube 12 in order to provide a better bearing surface for the rod 18 in the clamping position thereof. The end of the hollow tube 12 is closed by the use of an insert 40 which has an end cylindrical solid portion 42 which is formed with a bearing surface 44. The surface 44 of the insert 40 is oriented to be within the plane 34 and to form a continuation of the surface of the edge 30 when the insert is fixedly mounted within the hollow tube 12.

While the solid portion 42 of the insert 40 is cylindrical in configuration, the insert 40 is additionally provided with a semi-cylindrical extension 46 as shown which extends into the hollow tube 12 beyond the line of intersection 38 a distance which is approximately equal to the axial length of the probe end 26. The semi-cylindrical portion 46 of the insert 40 exhibits a flat surface 46a which slidingly abuts against the flat surface 26a of the rod end 26.

In order to fixedly secure the insert 40 within the end of the hollow tube as shown in FIG. 5, a hole 48 is provided in the wall of the hollow tube 12, which hole 48 is axially aligned with an annular groove or channel 50 in the solid portion 42. A solder or brazing compound 52 is provided which flows through the hole 48 and groove 50 when the probe end is suitably heated. After the insert 40 has been joined to the hollow tube 12, the end is ground to form a rounded tip 54 which facilitates insertion and probing in a narrow sinus.

The surface 28 is in a plane parallel to the plane 34 in which the surfaces 30 and 44 are disposed. This provides positive clamping over the entire surface ares 28 when an object such as a suture is clamped between the surfaces 28 and 44. It will be evident from an examination of FIG. 5 that the end portion 26 of the rod 18 is movable between a first clamping position wherein the end portion 26 abuts against the bearing surface portion 44 and a second releasing position wherein the end portion 26 is removed or spaced from the bearing surface portion 44. In this manner, the bearing surface portion 44 and the end portion 26 form a clamping device in the nature of a vise which can be opened and closed by relative movement therebetween along a direction parallel to the axis 10c of the probe 11.

According to an important feature of the present invention, locking means is provided, to be described particularly with reference to FIG. 3, for positively locking the relative axial positions of the hollow tube 12 and the clamping rod 18 in the clamping position to prevent inadvertent release of an object being clamped between the surfaces 28 and 44. In the presently preferred embodiment, the locking means also comprises adjusting means for adjusting the relative axial position of the rod 18 with respect to the hollow tube 12. The locking and adjusting means include a coaxial extension 56 of the finger grip 16, which extension is provided with external threads 60 over at least a portion thereof as shown.

The locking and adjusting means also includes an actuator nut or a clamp knob 62 which has an axial generally cylindrical blind hole or cavity 64 at least a portion of which is provided with internal threads 66 as shown. The end of the cavity 64 remote from the threaded end exhibits or defines a bearing surface 68 which is normal to the axis 10c of the instrument. The external threads 60 of the axial extension 56 and the internal thread 66 of the clamp knob 62 are threadedly engaged with each other so that turning of the actuator nut 62 about the axis of the instrument causes a linear or axial movement of the actuator nut relative to the finger grip 16 and therefore also relative to the hollow tube 12.

Engaging means in the form of a screw 70 extends through the actuator nut 62 and projects into the cavity 64 as shown to have the free end of the screw received within the annular groove or space 24 of the collar 22. Since the screw 70 is axially fixed on the actuator nut 62, the screw 70 follows the linear axial movements of the actuator nut and, since the screw 70 is captured within the collar 22, the collar and the clamp rod 18 similarly are made to follow the axial or linear movements of the actuator nut 62 relative to the hollow tube 12.

With the above-described construction, it should be clear that the clamp rod 18 can be moved axially with respect to the hollow tube 12 to move the clamping rod and portion 26 between the above-suggested clamping and releasing positions in the region of the hook 14. Advantageously, there is also provided a helical coil compression spring 72 which resiliently abuts between the free end of the extension 56 and the collar 22. The spring 72 biases the collar 22 and therefore the clamping rod 18 in a rearward direction away from the probing end. While the spring 72 also tends to maintain the collar 22 in abutment against the bearing surface 68 as does the screw 70, the function of the spring 72 is primarily to reduce backlash or hysteresis which may otherwise be present due to the clearances between the various parts. While a screw 70 has been shown and described to engage the collar 22, it should be clear that any radial-type pin which extends inwardly into the cavity 64 for being received or captured within the annular groove 24 may be utilized.

An important feature of the collar 22-screw 70 arrangement is that the screw 70 may be captured or coupled to the collar 22 for common axial or linear movement without corresponding coupling for turning or angular movements about the axis. Thus, while the actuator nut 62 and screw 70 simultaneously turn and move axially, the clamp rod 18 only follows along the axial direction to correspond to the axial movements of the actuator nut 62. The clamp rod 18 is prevented from angularly turning about the axis of the instrument by reason of the flat inside surface 46a inside the hollow tube 12 which flat surface is generally in a plane parallel to the axis as above described and the flat surface 26a which abuts against the flat surface 46a with some clearance only to permit slideable axial movements between the flat surfaces. Accordingly, the insert portion 46 cooperates with the clamping rod and portion 26 to permit axial slideable movements of the clamp rod but prevents rotation of the clamp rod within the hollow tube 12. This arrangement insures that the surfaces 28 and 44 forming the clamping surfaces are always arranged in substantially parallel planes for maximum clamping effectiveness. Additionally, prevention of turning of the clamp rod 16 minimizes the damage which the clamp rod can do to an object being clamped due to the shearing forces which a rotating clamp rod would normally exert. For this reason, the arrangement of the present invention preserves the integrity of the object clamped and the only precaution which must be taken is that of not excessively advancing the surface 28 towards the surface 44 when an object is disposed therebetween. Excessive clamping or application of pressure on an object between the surfaces 28 and 44 can normally be minimized by sensing the resistance of the clamping rod 18 to further advancement when the actuator nut 62 is being turned, such sensing of resistance being developed by experience from using the Instrument.

As described above, turning of the actuator nut 62 causes the clamp rod 18 to move axially since it is coupled to the actuator nut by means of the collar 22 and screw 70. The threaded engagement between the actuator nut 62 and the axial extension 56 represents a mechanical advantage which permits the application of substantial axial forces to the clamp rod 18 upon turning of the actuator nut 62. Since relatively small forces used to turn the actuator nut 62 can be translated into relatively high axial forces on the clamp rod 18, there is some danger that the actuator nut 62 can continue to be turned somewhat even after the surfaces 28 and 44 are in abutment against each other. Clearly, any further turning of the actuator nut 62 which advances the clamp rod 18 after such engagement of the surfaces 28 and 44 may result in damage to the hollow tube 12 as well as the clamp rod 18 by causing one or the other or both of these coacting elements to become bent or deformed. To prevent such excessive advancement of the clamp rod 18 beyond a predetermined or desired point, there is provided a stop means for preventing turning of the actuator nut 62 beyond a predetermined axial position to prevent excessive axial movement of the actuator nut 62 and, therefore, the elongate rod 18, with respect to the hollow tube 12. The stop means in accordance with the presently preferred embodiment is in the nature of a stop nut 76 which is provided with internal threads 78 which are threadedly engaged with the external threads 60 of the extension 56. As best shown in FIG. 3, the stop nut 76 can be axially positioned on the threaded portion of the extension 56 and fixed in the axial position on the extension 56 by means of a set-screw arrangement 80. Now, the actuator nut 62 and the clamp rod 18 can only be advanced in the direction of the probing end 10a until the actuator nut 62 engages and abuts against the stop nut 76 as shown in FIG. 3. By variously axially positioning the stop nut 76 on the extension 56, the minimum spacing between the surfaces 28 and 44 can therefore be controlled. In accordance with the presently preferred embodiment, it is advantageous that the stop nut 76 be so positioned on the extension 56 that the actuator nut 62 engages the stop nut 76 simultaneously with the engagement or contact between the surfaces 28 and 44 in the region of the hook 14. Clearly, with such an initial adjustment of the stop nut 76, the clamp rod 18 cannot be excessively advanced so as to cause damage to the instrument in the area of the hook 14 while permitting the clamping of the smallest of objects even approaching the dimensions of those of a human hair.

While a surgical instrument only including a hollow tube 12 and a clamp rod 18 is useful for certain procedures, to be more fully described below, the instrument 10 of the present invention is advantageously provided with cutting means for cutting an object clamped by the probe means or hollow tube 12 and clamping means or clamp rod 18. Referring particularly to FIGS. 3 and 5, the instrument 10 is shown to be provided with an elongate external sleeve or rotary cutter element 82. The outside surface of the hollow tube 12 is cylindrical and has a circular cross-section along its longitudinal length. The inside surface of the outside cutting sleeve or rotary cutter element 82 is similarly dimensioned to the outside surface of the hollow tube 12 so that the cutting sleeve 82 matingly receives the hollow tube 12 with little clearance therebetween but with sufficient clearance to permit relative axial and angular movements between the hollow tube 12 and the cutting sleeve 82. The end 82a of the sleeve 82 which is remote from the probing end 10a is fixedly joined to a cutter actuator or control member 84 which is mounted on a forwardly projecting axial and cylindrical extension 86 of the finger grip 16. The cutter actuator 84 is provided with a first axial and cylindrical cavity or hole 88 of a small diameter and a coaxial cylindrical cavity or hole 90 of a large diameter as shown in FIG. 3 for receiving the extension 86 therein.

The cylindrical extension 86 in the presently preferred embodiment is provided with means to be described which prevents undesirable relative axial movements between the hollow tube 12 and the cutter element 82.

The axial and cylindrical extension 86 is in the presently preferred embodiment provided with a circumferential slot 92 which, as shown in FIGS. 1, 3 and 6, is advantageously a helical slot coaxial with the axis 10c. A screw 94 is threadedly received within a hole on the cutter actuator 84 and the free end of the screw is received within the helical groove 92 to form a cam and follower arrangement wherein relative turning between the finger grip 16 and the cutter actuator 84 results in a simultaneous axial displacement between the same.

The length of the groove 92 is selected to prevent excessive relative angular displacement between the finger grip 16 and the cutter actuator 84. A helical spring 96, having a leg 96a received within a hole of the cutter actuator 84 and a leg 96b received within a hole of the finger grip 16 is so placed so as to maintain the screw 94 in abutment against one end of the groove or slot 92. Turning of the cutter actuator against the action of the spring 96 permits relative angular displacement between the cutter actuator 84 and the finger grip 16 to an extent permitted by the other end of the groove 92. In effect, the ends of the groove serve as stops which effectively engage the captured end of the screw 94 or some other pin means used for the purpose. With this construction, therefore, the cutter actuator 84 always returns to its normal position, which, as will become evident from the description that follows, corresponds to the non-cutting position of the rotary cutting element 82.

As described above, the cutter actuator element 84 is coaxially and rotatably mounted on the extensions 86 of the finger grip 16. The cutter actuator 84 includes engaging means for engaging and gripping the cutter element 82 to cause simultaneous turning of the cutter element 82 and cutter actuator 84 about the axis 10c relative to the hollow tube 12. The aforementioned engaging means of the cutter actuator 84 is in the nature of an externally threaded collet 96 which projects forwardly of the cutter actuator 84 along the axis of the instrument as shown in FIG. 3. A cutter collet lock nut 98 is threadedly mounted on the collet 96 and has a gripping characteristic that tightening of the lock nut 98 causes the collet fingers to increasingly clamp the portion of the cutter element or sleeve 82 which is disposed between the fingers of the collet 96. With such an arrangement, the lock nut 98 may be loosened and the cutting sleeve 82 may be selectively positioned with respect to the hollow tube 12 and hook 14 prior to retightening of the lock nut 98 for the purpose of fixing the selected relative positions of the cutting sleeve 82 and hollow tube 12.

As should be evident from the above description, the lock nut 98 is used to position the cutting sleeve 82 in an initially desired non-cutting position. This non-cutting condition is one wherein the cutter actuator 84 is in its normal angular position with respect to the finger grip 16 by reason of the biasing action of the helical spring 96. Angular displacement of the cutter actuator 94 against the action of the helical spring 96 causes simultaneous linear translation or movement of the cutter actuator 84 in a direction away from the finger grip 16 to increase the space 99 therebetween. Such axial advancement of the cutter actuator 84 causes corresponding axial advancement of the cutting sleeve 82 since the cutting sleeve is fixedly coupled to the cutter actuator 84 by means of the collet 96-lock nut 98 arrangement.

As best shown in FIGS. 5 and 7, the cutting sleeve or rotary cutting element 82 is provided at the probing end thereof with a cutting edge 100 which is essentially coextensive with the outside surface of the hollow tube 12 to form little clearance therebetween. The rotary cutting element 82 is mounted for rotary movement relative to the hollow tube 12 about the axis 10c, the cutting edge 100 sweeping the outside surface of the hollow tube 12 in the region of the hook 14 during rotary movement of the cutter element 82 to cut an object clamped between the surfaces 28 and 44. As best shown in FIG. 7, the cutting edge 100 of the rotary element 82 is in the nature of a circular or helical edge which progressively cuts successive axial portions of the clamped object with continued turning of the rotary element 82.

As suggested above, the external dimensions of the hollow tube 12 and the internal dimensions of the cutting sleeve 82 are so selected so that there is little clearance therebetween while being sufficient to permit relative turning between the hollow tube and external sleeve. However, in order to increase the cutting effectiveness of the instrument, there is advantageously provided indentation means 101 in the cutter sleeve 82, for further reducing the clearance between the hollow tube 12 and the cutting edge 100 to substantially form a force or interference fit at the cutting edge to improve the cutting characteristics thereof.

As described above, the length of the helical and circumferential slot 92 in the coaxial extension 86 is selected to limit relative turning movements between the finger grip 16 and the cutter element 82. As will become evident, the cutter element 82 is, with such an arrangement, movable between a first relative position wherein the cutting edge 100 is circumferentially beyond the open area of the hook or wedge-shaped cutout 14 to fully expose the hook, and a second relative position wherein at least a portion of the cutting edge 100 has swept over the area of the hook to cover the same as best shown in FIG. 7 whereby a clamped object extending between two opposing points on the face of the hollow tube 12 is cut at one of these points while the other is maintained clamped at the other of the points. Referring particularly to FIG. 7, the hook 14 is shown to be in the form of a crochet-type hook which extends between two opposing points on opposite sides of a plane passing through the axis of the instrument, the exposed side 14a being one side of such plane of symmetry and another side of the hook 14b being on the other side of such a plane. Accordingly, an important feature of the present invention is that the cutter element 82 be initially adjusted and mounted for turning relative to the hollow tube 12 to sweep only over a portion of the hook 14 or only over one of the sides thereof to assure cutting of the clamped object. However, the rotary knife edge 100 must not be rotatable so as to sweep over both sides 14a and 14b of the hook 14 since such excessive relative rotation would cause the rotary edge 100 to cut the clamped object at both clamped points and this may result in the need for minor surgery in order to retrieve the suture. By maintaining the suture clamped at one end or side of the instrument, the object may be convenienly and easily retrieved from deep within the sinus to therefore eliminate the necessity for such surgery.

As described above, displacement of the cutter actuator 84 relative to the finger grip 16 causes both angular as well as linear or axial movement of the cutting sleeve 82 relative to the outer sleeve 12. These two relative movements are respectively designated by the reference numerals 102 and 104 in FIG. 7, the combination of these two simultaneous movements substantially improving the cutting characteristics of the rotary knife. The suture 106 shown in FIG. 7 is initially clamped between the bearing surface 44 and the surface 28 of the rod end 26. Simultaneous turning and advancement of the cutting sleeve 82 is effective to cut the suture 106 at one side 14b of the hook to release the cut portion 106b of the suture. However, the helical and circumferential slot 92 prevents excessive angular displacement of the rotary edge 100 so that the clamped portion 106a of the suture 106 remains to be clamped when the rotary knife has move to the end of its travel.

Initial adjustment of the instrument 10 is important and the initial relative axial and angular displacements between the hollow tube 12, clamping rod 18 and cutting sleeve 82 must be made to provide optimum performance.

In order to test whether the hook 14-clamp rod 18 arrangement is operating satisfactorily, a 6 inch length of suture, for example, is joined with a surgical knot. It is then placed around a post and the suture is hooked, clamped by turning the actuator nut 62, held taut and the cutter actuator 84 is then rotated relative to the finger grip 16 through full travel until the suture is cut. This should not take more than three or four turns of the cutting control 84. After the suture is cut, an attempt should be made to pull the suture out of the grasp of the hook 14. A number 13 silk suture should break before it can be pulled from the grasp of the hook. The adjustment which controls this is the stop nut 76.

The stop nut 76 is secured in position, for example, by an Allen-type set screw arrangement. This adjustment is a very important adjustment. If it is set too far to the rear of the instrument, the clamping rod 18 will not press sufficiently hard against the bearing surface 44 to hold the suture securely. On the other hand, if the stop nut 76 is set too far forward, the clamp rod 18 will not only attach or contact the surface 44, it will push it forward and deform it. The proper means of adjustment is to loosen the Allen set screw extending through the threaded hole 80 and rotate the stop nut 76 all the way forward. Then, the actuator nut 62 is rotated to axially advance the same until solid resistance is felt, this indicating that the clamp rod 18 is snug against the bearing surface 44. This can be verified by placing a very fine suture in the hook 14 and making sure that it is grasped securely. Of course, care must be taken not to over-tighten the actuator nut 62. Once the position of the actuator 62 has been found, it is firmly held in place and the stop nut 76 is rotated in the direction of the actuator nut 62 until it is in contact with the same. The set screw extending through the threaded hole 80 is then securely tightened to hold the stop nut 76 in this position. This should complete the adjustment of the stop nut.

The other adjustment of the invention prior to use is the adjustment of the cutting sleeve 82 with respect to the hook 14 to provide satisfactory cutting without cutting sutures, for example, at both clamped ends thereof. Two adjustments can be made after the collet lock nut 98 is loosened. One adjustment is the relative angular position of the sleeve 82 about the axis with respect to the hollow tube 12, and the other adjustment is of the lateral or axial relative position therebetween. At the starting point, the forwardmost tip of the cutting edge 100 should be approximately one-tenth of an inch from the tip of the hook 14. The right hand side, for example, of the blade 100 which is advantageously a non-sharpened side, should be substantially flush with the right hand part of the edge 32. In this position, when rotated slowly, the sharp portion of the blade should not sweep over the right hand side of the hook 14. The length of the circumferential and helical slot 92 should be selected so that in the maximum travel of the cutting sleeve 82, the sharpened portion of the blade should not move closer than approximately 0.04 inches to the extreme portion or side of the hook 14a. If the sharpened portion of the blade moves too close to the right hand side of 14a of the hook in the maximum travel position of the rotary sleeve 82, then the blade should be moved back laterally as required.

If the cutting edge 100 does not cut the suture properly, or only partially cuts the strands, this may indicate that the clearance between the edge 100 and the left hand portion or side 14b of the hook 14 must be decreased. This may be adjusted by providing an interference fit, such as the two blades of a scissors must fit in order to cut properly. If an indentation 101 has not yet been provided, a center punch may be used to provide such indentation to produce the interference fit. The indentation is applied as close to 180° as is practical from the portion of the blade 100 which touches the left hand edge of the hook 14. The punch will cause a small indentation which will force the blade closer against the cutting edge 100 and result in a proper cut.

While the materials from which the instrument 10 is made is not critical, the instrument parts or elements are advantageously made of stainless steel of the type used for surgical instruments.

The operation of the instrument 10 will now be described. The primary function of the instrument 10 is as a subcutaneous suture extracting device. Although other functions of the device will be described hereafter. Referring to FIG. 8, the instrument 10 is adjusted to open the hook area by fully withdrawing the clamping rod 18 from the region of the hook 14. This is achieved by rotating the clamping knob or actuator nut 62, for example, in a counterclockwise direction approximately three complete turns.

Referring to FIGS. 8 and 9, the instrument 10 is carefully inserted past the skin layers 108, 110 and 112 to bring the probing free end or hook of the instrument into the base 114 of a sinus 116. Once the probe 11 has been carefully inserted into the suture granuloma sinus, it is advantageously held by the slender portion of the probe 11 for maximum sensitivity. The paths or necks 116 of the sinus will generally lead one to the suture which is often found at the base 114 of the sinus. Very gentle insertion of the hook to the maximum depth of the sinus will often guide the hook directly to the suture. The open portion of the hook is gently scraped against the walls of the sinus in an attempt to snag the suture. The cavity is carefully explored by gradual axial rotation and repeated withdrawal until the suture is hooked. Since the handle grip 16 is fixedly joined to the hollow tube 12 and the hook 14, suitable marker or indicating means may be provided on the handle grip 16 to indicate the direction of the opening.

Once a feeling of resistance to withdrawal of the hook is encountered, the hook should be maintained with gentle tension and the clamping rod 18 should be closed by rotating the clamping knob 62 clockwise (at 118) until it is snug against the stop nut 76. In this connection, it is important to grasp the instrument by the finger grip 16 while turning the clamping knob 62 in order to avoid the turning or relative rotation of the cutting sleeve 82 so that the suture is not inadvertently cut before it is secured in the hook 14. The hook is then tugged gently to make certain that the suture is well engaged. If the hook comes free it indicates that the suture itself was not hooked but only a piece of scar tissue was snagged.

Now, the suture is cut by rotating the cutter actuator 84 while securely holding the finger grip 16. The cutter actuator 84 is turned fully clockwise (at 120), which is approximately one-half a turn, and then the cutter actuator 84 is released. To be certain of having a complete cut, it may be necessary to rotate the cutter actuator and, therefore, the blade 100, two or three times. Finally, the hook is withdrawn with the suture. Should the hook come out without a suture this indicates that a piece of scar tissue, rather than a suture had been engaged. This does not representation a malfunction of the hook and it appears quite frequently. Several attempts at hooking and extracting may be necessary. Clamping of the suture is shown in FIG. 9 while cutting and extraction of the suture is shown in FIG. 10.

Clearly, in order to avoid cutting of both ends of the clamped suture, the circumferential length of the helical groove 92 should be accurately selected. While the groove 92 may extend over an angular displacement at 180°, shorter slots of less than about 140° of angular displacement or circumferential length permits less critical adjustment of the cutting sleeve 82 to permit cutting of the suture at only one clamped end thereof.

An important design consideration of the instrument 10 is the axial position of the hook 14 relative to the tip 54 of the instrument. Advantageously, the hook 14 is axially spaced as close to the tip 54 as possible. This facilitates the probing procedure and the engagement of deeper sutures. Additionally, placing the hook 14 as close as possible to the tip 54 of the instrument permits probing for the suture with minimal penetration of muscle tissues which muscle penetration may result in reflex movements in the patient as well as pain to the patient. Additionally, as shown in FIGS. 1 and 2, the various actuating or control elements or members at the hand-held end 10b of the device 10 are generally smooth and devoid of recesses. The various actuating elements, such as the finger grip 16, actuator nut 62, stop nut 76, cutter actuator 84 and lock nut 98 are provided with smooth, generally flat surfaces (16a, 16b, 84a, 84b) which facilitate the gripping of the same without permitting excessive collection of materials. Although not shown, each of the actuating or control element at the instrument end 10b are provided with markings or indicia which indicate to the user the desired directions of rotation or movement to effect the desired function or result.

The instrument 10, including the hollow tube 10, clamp rod 18 and cutting sleeve 82, is primarily a subcutaneous suture extractor as described above. However, it should be evident to one skilled in the art, that the instrument which results when the cutting sleeve 82 is eliminated may still be used to perform various procedures. For example, only using the hollow tube 12 and clamp rod 18, the probe may be inserted through a sinus as above described to grip and clamp a piece of tissue which can be extracted for the purpose of performing a biopsy thereon. In this sense, the device may be used as a subcutaneous tissue biopsy sampler. Additionally, the clamping arrangement of the hook 14 of the clamp rod 18 may be used to locally introduce or remove subcutaneously a medicament such as an antibiotic or anaesthetic. A small pill or small grains of a medicament can, for example, be clamped between the surfaces 28 and 44 and released subcutaneously by separation of the surfaces. A liquid-filled capsule can also, for example, be introduced subcutaneously and ruptured by further tightening of the clamping rod 18 to release a medicament locally.

In all the aforementioned applications of the instrument 10, the tip 54 may be only slightly rounded as shown in FIGS. 1, 2, 3 and 7-10. However, by providing a more pointed and sharpened tip 54' as shown in FIG. 11, the probe 11 may be used to puncture the skin as does a needle or hypodermic syringe instead of introducing the probe through a sinus.

When the clamp rod 18 is received within the hollow tube 12 with small clearance, extraction of the clamp rod 18 from the hollow tube 12 produces a well known suction at the open end in the region of the hook 14 which may be used to extract fluid samples from below the skin layers. In the same way, the hollow tube can initially be filled with the fluid which can be discharged subcutaneously by advancing the clamp rod 18 through the hollow tube in the direction of the hook 14. In this connection, by totally withdrawing the clamp rod 18 from the hollow tube 12 and removing the actuator nut 62, this exposes the end of the hollow tube 12 when the hollow tube extends somewhat beyond the extension 56 to form a nipple 74, the nipple 74 may be connected to a source of fluid which can be forced through the hollow tube 12 to be discharged through the hook opening 14. Such an arrangement permits subcutaneous introduction or extraction of fluids.

It should be clear that the surgical instrument 10 of the present invention can beutilized for several various functions and procedures, the primary one of which is the subcutaneous extraction of sutures. However, by eliminating one or more of the elements of the device or instrument 10, additional function procedures may be achieved as suggested above.

It is to be understood that the foregoing description of the various embodiments illustrated herein is exemplary in nature and various modifications to the embodiments shown herein may be made without departing from the scope and spirit of the invention.

What is claimed is:

1. A multi-purpose surgical instrument for subcutaneous use comprising probe means in the nature of an elongate and generally slender member having a generally uniform transverse cross-section along the longitudinal axis thereof and having a bearing surface portion at the probing free end thereof; and clamping means arranged for movement in a direction generally parallel to said axis of said probe means and having an end portion thereof movable between a first clamping position wherein said end portion abuts against said bearing surface portion and a second releasing position wherein said end portion is removed or spaced from said bearing surface portion, whereby said bearing surface portion and end portion together form a clamping device in the nature of a vice which can be opened and closed by relative movement therebetween along a direction generally parallel to said axis of said probe means.

2. A surgical instrument as defined in claim 1, further comprising locking means for positively locking the relative axial positions of said prove and clamping means in said first clamping position to prevent inadvertent release of an object being clamped.

3. A surgical instrument as defined in claim 1, wherein said probe means comprises an elongate hollow tube and said clamping means comprises an elongate rod coaxially disposed within said hollow tube for slidable movement therein.

4. A surgical instrument as defined in claim 3, wherein the instrument is adapted to be hand-held and hand operated, and further comprising coaxial finger gripping means fixedly joined to said hollow tube at the hand-held end thereof remote from said probing free end, said elongate rod having a length greater than the length of said hollow tube to extend beyond the hand-held end thereof; and adjusting means mounted on said finger gripping end for engaging said rod extension and for selectively adjusting the relative axial positions of said hollow tube and elongate rod.

5. A surgical instrument as defined in claim 4, wherein said elongate rod portion extending beyond said hollow tube is provided with an engageable portion, said finger gripping means being provided with a coaxial externally threaded extension projecting in a direction away from said probing free end, said adjusting means comprising an internally threaded actuator nut threadedly engaged with said threaded extension and having a coaxial cylindrical blind cavity defining a bearing surface; and engaging means for engaging said engageable portion to maintain the same substantially in abutment against said cavity bearing surface, whereby said elongate rod axially follows said actuator nut as said threaded actuator nut moves axially on said threaded extension simultaneously with turning of said nut about said axis.

6. A surgical instrument as defined in claim 5, wherein said engageable portion comprises a cylindrical collar having a coaxial annular groove, and same engaging means comprises a radial pin on said actuator nut projecting inwardly to be received within said groove, whereby said pin causes said elongate rod to axially follow said actuator nut as said actuator nut is turned and moved axially due to the threaded engagement with said threaded extension.

7. A surgical instrument as defined in claim 6, wherein said pin is in the nature of a screw.

8. A surgical instrument as defined in claim 6, further comprising a compression spring within said blind cavity for resiliently acting between said threaded extension and said elongate rod engageable portion to bias the same against said bearing surface to minimize hysteresis during reversals of rotation of said actuator nut.

9. A surgical instrument as defined in claim 5, further comprising a stop means for limiting turning of said actuator nut beyond a predetermined axial position to prevent excessive axial movement of said actuator nut and elongate rod with respect to said hollow tube in movements from said second to said first positions.

10. A surgical instrument as defined in claim 9, wherein said stop means comprises a stop nut on said threaded extension which is selectively positionable on said threaded extension to abut against said actuator nut to prevent excessive advancement of the same at a preselected axial position on said threaded extension, whereby the maximum gripping pressures between said probing free end bearing surface and said elongate rod end portion may be controlled.

11. A surgical instrument as defined in claim 5, further comprising means for preventing rotation of said elongate rod during axial slidable movements thereof.

12. A surgical instrument as defined in claim 11, wherein said means for preventing rotation comprises a flat inside surface of said hollow tube which flat surface is generally in a plane parallel to said axis, said elongate rod end portion having a flat surface generally parallel to said axis which abuts against said flat surface of said hollow tube with clearance only to permit slidable axial movements between said flat surfaces.

13. A surgical instrument as defined in claim 3, wherein said external dimensions of said elongate rod and internal dimensions of said hollow tube are selected to be substantially similar to provide a small clearance fit therebetween, whereby fluid may be subcutaneously discharged or retrieved by suitable movement of said elongate rod within said hollow tube to thereby function as a syringe.

14. A surgical instrument as defined in claim 1, wherein said probing free end is provided with a sharply pointed tip, whereby said instrument may be used as a hypodermic needle for piercing the upper skin layers.

15. A surgical instrument as defined in claim 1, wherein the instrument is a subcutaneous suture remover, and said probe means is provided with a crochet-type hook which includes said bearing surface portion at said probing free end.

16. A surgical instrument as defined in claim 3, wherein said hollow tube is provided at the end thereof remote from said probing free end which means for receiving and introducing fluid into said hollow tube, whereby fluid may be introduced or removed subcutaneously.

17. A surgical instrument as defined in claim 1, wherein said probe means bearing surface portion and said clamping means end portion are mounted for relative movement to provide a separation therebetween which is at least comparable to the cross-sectional dimensions of said hollow tube to permit an object to be gripped by said bearing surface and end portions and be introduced or removed subcutaneously.

18. A surgical instrument as defined in claim 3, wherein said hollow tube is formed at said probing free end with a crochet-type hook suitable for engaging subcutaneous tissue, whereby at least a portion of such subcutaneous tissue may be engaged by said hook and clamped to permit removal of the same to thereby serve as a biopsy sampler.

19. A surgical instrument as defined in claim 3, wherein said hollow tube is formed at said probing free end with a crochet-type hook configured and dimensioned to permit engagement of subcutaneous matter during probing with said hook, said hook generally being in the shape of a wedge-shaped transverse cutout which opens in a direction away from said probing free end and in the direction of the major length portion of said hollow tube.

20. A surgical instrument as defined in claim 19, wherein said wedge-shaped cutout in said hollow tube is defined by a pair of arcuate edges, each of which respectively lies in one or two planes which intersect in the region of said axis along a line substantially normal to said axis and each of which planes forms a different acute angle with said axis and the major portion of said hollow tube.

21. A surgical instrument as defined in claim 20, wherein said line of intersection of said two planes passes through said axis and is coincident with a diameter of said hollow tube.

22. A surgical instrument as defined in claim 1, further comprising cutting means for cutting an object clamped by said probe and clamping means at only one clamped point at the clamping area, whereby at least a portion of the cut object is retained after cutting to permit subcutaneous extraction of that portion of the object which remains to be clamped.

23. A surgical instrument as defined in claim 22, wherein said clamping means includes locking means for positively locking the relative axial position of said probe and clamping means to assure that at least a portion of an object to be subcutaneously extracted remains to be clamped after cutting and to prevent inadvertent release of the clamped object portion during extraction.

24. A surgical instrument as defined in claim 22, wherein said probe means comprises an elongate hollow tube, the outside surface of which is circular in cross-section along its longitudinal length, and wherein said cutting means comprises a rotary cutter element which includes a cutting edge which surrounds at least a portion of said hollow tube in the region of said probing free end thereof, said cutting edge being substantially coextensive with said outside surface to form little clearance therebetween and being mounted for rotary movement relative to said hollow tube about said axis, said cutting edge sweeping said probing free end during rotary movement thereof to cut an object clamped by said bearing surface and end portions.

25. A surgical instrument as defined in claim 24, wherein the instrument is adapted to subcutaneously extract sutures, said hollow tube being formed at said probing free end with a crochet-type hook configurated and dimensioned to permit subcutaneous engagement of sutures during probing with said hook, said hook generally being in the shape of a wedge-shaped transverse cutout which opens in a direction away from said probing free end and in the direction of the major length portion of said hollow tube.

26. A surgical instrument as defined in claim 25, wherein said wedge-shaped cutout in said hollow tube is defined by a pair of arcuate edges each of which respectively lies in one of two planes which intersect in the region of said axis along a line substantially normal to said axis and each of which planes forms a different acute angle with said axis and the major portion of said hollow tube.

27. A surgical instrument as defined in claim 24, wherein said rotary cutter element is in the nature of an elongate external sleeve which has an inside surface of circular cross-section along its longitudinal length, said inside surface having dimensions substantially corresponding to the outside surface of said hollow tube to provide little clearance therebetween said clearance being sufficient to permit relative turning between said hollow tube and external sleeve.

28. A surgical instrument as defined in claim 24, wherein said cutter element is provided with indentation means for reducing the clearance between said hollow tube probing free end and said cutting edge to substantially form an interference-fit at said cutting edge to improve the cutting characteristics thereof.

29. A surgical instrument as defined in claim 24, wherein said probe and clamping means together form a crochet-type hook clamping arrangement which extends between two opposing points on opposite sides of a plane passing through said axis, said cutter element being mounted for turning relative to said hollow tube to sweep only over a portion of said clamping arrangement between said opposing points to assure cutting of a clamped object only at one of said opposing points, whereby at least a portion of the clamped object continues to be clamped subsequent to cutting.

30. A surgical instrument as defined in claim 29, wherein the instrument is adapted to be hand-held and hand-operated, and further comprising coaxial finger gripping means fixedly joined to said hollow tube at the hand-held end thereof remote from said probing free end; and cutter actuator means connected to said cutter element and mounted on said finger gripping end for preventing undesirable relative axial movements between said nollow tube and said cutter element.

31. A surgical instrument as defined in claim 30, wherein said finger gripping means is provided with a coaxial extension projecting in the direction of said probing free end, said cutter actuator means being coaxially and rotatably mounted on said coaxial extension, said cutter actuator means including engaging means for engaging and gripping said cutter element to cause simultaneous turning of said cutter element and cutter actuating means about said axis relative to said hollow tube, and limiting means for limiting relative turning between said hook clamping arrangement and said cutter element between a first relative position wherein said cutting edge is circumferentially beyond said two opposing points to fully expose said hook clamping arrangement and a second relative position wherein at lease a portion of said cutting edge is disposed between said two opposing points to only partially cover said hook clamping arrangement, whereby a clamped object extending between said two opposing points remains clamped subsequent to movement from said first to second relative positions.

32. A surgical instrument as defined in claim 31, wherein said limiting means comprises a circumferential slot in said coaxial extension, and follower pin means on said actuator means slidably received within said slot, said slot having circumferentially opposing ends disposed to limit relative turning movements between said finger gripping means and said cutter element.

33. A surgical instrument as defined in claim 31, further comprising biasing means for normally maintaining said hook clamping arrangement and cutter element in said first relative position.

34. A surgical instrument as defined in claim 32, wherein said slot is a helical slot coaxial with said axis, whereby relative turning between said finger gripping means and said cutter element provides an axial or linear as well as an angular displacement therebetween as said pin means moves in and follows said helical slot, whereby the combination of said relative linear and angular movements enhances the cutting characteristics of the instrument.

35. A surgical instrument as defined in claim 30, wherein said cutter actuating means includes adjusting means for adjusting the normal non-cutting axial position of said cutter element relative to said hollow tube and the normal angular non-cutting position of said cutter element relative to said hook clamping arrangement.

36. A surgical instrument as defined in claim 35, wherein said adjusting means comprises a collet-lock nut arrangement which receives a portion of said cutter element in a selected position and grips said cutter portion by tightening said lock nut on said collet.

37. A subcutaneous suture extraction surgical instrument comprising:
  a. an elongate and generally slender circular hollow tube having a longitudinal axis and provided with a crochet-type hook at a probing end thereof, said hook having a bearing surface portion generally facing the hand-held end thereof remote from said probing ends;
  b. a finger grip fixedly joined to said hand-held end of said hollow tube and configurated to facilitate gripping and handling of said hollow tube;
  c. an elongate rod having an end portion and mounted within said hollow tube for slideable axial movements relative to said hollow tube between a clamping position wherein said end portion is in abutment against said bearing surface portion and a releasing position wherein said end portion is spaced from said bearing surface portion;
  d. adjusting means mounted on said finger grip and coupled to said elongate rod for selectively adjusting the spacing between said bearing surface portion and said end portion to permit movement of said rod between said clamping and releasing positions, said bearing surface portion and end portion together forming a clamping device in the nature of a vice which can be opened and closed by relative movement between said hollow tube and elongate rod along a direction generally parallel to said axis;
  e. a rotary cutter element in the nature of an outside sleeve which is coextensive with the outside surface of said hollow tube and covers the same substantially over the entire length thereof, said outside sleeve being mounted on said hollow tube for relative angular or rotary and axial movements with respect to said hollow tube and having circular cutting edge in the region of said hook, said cutter element being movable between a non-cutting position wherein said cutting edge fully exposes said hook for probing and engaging a suture, and a cutting position wherein said cutting edge sweeps over at least a portion of said hook to cut a suture clamped by said hollow tube bearing surface portion and said rod; and
  f. a cutter actuator fixedly connected to said cutter element at the end thereof remote from said cutting edge and being mounted on said finger grip for movement relative thereto between first and second portions respectively corresponding to said cutting and non-cutting positions of said cutter element, whereby relative movement between said hollow tube hook and cutter element cutting edge may be affected by corresponding relative movement between said finger grip and cutter actuator to cut a suture clamped within said hook by said elongate rod, and whereby subcutaneous hooking, clamping and cutting procedures can be performed by controlling said adjusting means and cutter actuator relative to said finger grip at the hand-held end of the instrument.

* * * * *